US012349954B2

United States Patent
Zhang et al.

(10) Patent No.: US 12,349,954 B2
(45) Date of Patent: Jul. 8, 2025

(54) PULSED ELECTRIC FIELD MULTI-ELECTRODE ABLATION APPARATUS

(71) Applicant: ACCUPULSE MEDICAL TECHNOLOGY (SUZHOU) CO., LTD., Jiangsu (CN)

(72) Inventors: Xiangming Zhang, Jiangsu (CN); Youfu Yue, Jiangsu (CN); Lei Zhang, Jiangsu (CN)

(73) Assignee: ACCUPULSE MEDICAL TECHNOLOGY (SUZHOU) CO., LTD., Jiangsu (CN)

( * ) Notice: Subject to any disclaimer, the term of this patent is extended or adjusted under 35 U.S.C. 154(b) by 0 days.

(21) Appl. No.: 18/804,616

(22) Filed: Aug. 14, 2024

(65) Prior Publication Data
US 2024/0398459 A1 Dec. 5, 2024

Related U.S. Application Data

(63) Continuation of application No. PCT/CN2022/107912, filed on Jul. 26, 2022.

(30) Foreign Application Priority Data

Mar. 16, 2022 (CN) .......................... 202210258360.6

(51) Int. Cl.
A61B 18/00 (2006.01)
(52) U.S. Cl.
CPC ...... *A61B 18/00* (2013.01); *A61B 2018/0016* (2013.01); *A61B 2018/00577* (2013.01);
(Continued)
(58) Field of Classification Search
CPC ............ A61B 18/00; A61B 2018/0016; A61B 2018/00577; A61B 2018/00672;
(Continued)

(56) References Cited

U.S. PATENT DOCUMENTS 6,264,653 B1 7/2001 Falwell
2013/0296679 A1* 11/2013 Condie ................ A61B 5/6856
600/374
2018/0228528 A1* 8/2018 Fraasch ............. A61B 18/1206

FOREIGN PATENT DOCUMENTS

CN 103379873 10/2013
CN 106061421 10/2016
(Continued)

OTHER PUBLICATIONS

International Search Report issued Dec. 13, 2022, by CNIPA as the ISA, in International Application No. PCT/CN2022/107912.

*Primary Examiner* — Linda C Dvorak
*Assistant Examiner* — Christine A Dedoulis
(74) *Attorney, Agent, or Firm* — Wenderoth, Lind & Ponack, L.L.P.

(57) ABSTRACT

A pulsed electric field multi-electrode ablation apparatus, comprising: an ablation catheter (1), which comprises a catheter (1100), and three or more electrodes that are arranged on the catheter (1100); a pulse energy generator, which is electrically connected to the electrodes; and an impedance measurement component, which is electrically connected to the electrodes, wherein the pulse energy generator can generate a pulse wave between any two electrodes; and the impedance measurement component can measure the impedance between any electrodes and/or between any electrode and an external electrode. The pulsed electric field multi-electrode ablation apparatus can provide accurate information of an electrode attachment condition for a user, such that the electrode attachment condition can be adjusted to an ideal state, and after a pulse wave is released between the electrodes by means of the pulse energy generator, a more ideal treatment effect can be obtained.

10 Claims, 4 Drawing Sheets

(52) U.S. Cl.
CPC .............. *A61B 2018/00672* (2013.01); *A61B 2018/00761* (2013.01); *A61B 2018/00767* (2013.01); *A61B 2018/00875* (2013.01)

(58) Field of Classification Search
CPC ........... A61B 2018/00761; A61B 2018/00767; A61B 2018/00875
See application file for complete search history.

(56) References Cited

FOREIGN PATENT DOCUMENTS

| | | |
|---|---|---|
| CN | 110234289 | 9/2019 |
| CN | 110693605 | 1/2020 |
| CN | 111728693 | 10/2020 |
| CN | 113143447 | 7/2021 |
| CN | 214208476 | 9/2021 |
| CN | 113576647 | 11/2021 |
| CN | 113648045 | 11/2021 |
| CN | 113768612 | 12/2021 |
| CN | 113768616 | 12/2021 |
| CN | 113907880 | 1/2022 |
| CN | 114711958 | 7/2022 |
| EP | 4 378 409 | 6/2024 |
| WO | 2012/106100 | 8/2012 |
| WO | 2015/081420 | 6/2015 |
| WO | 2018/140593 | 8/2018 |

\* cited by examiner

PULSED ELECTRIC FIELD MULTI-ELECTRODE ABLATION APPARATUS

CROSS-REFERENCE TO RELATED APPLICATIONS

The present application is a continuation of PCT/CN2022/107912, filed Jul. 26, 2022, and claims the benefit of CN 202210258360.6, filed Mar. 16, 2022, the entire contents of which are hereby incorporated by reference.

TECHNICAL FIELD

The present application relates to the technical field of medical devices, and in particular to a pulsed electric field multi-electrode ablation apparatus.

BACKGROUND

Generally, the ablation energy in the catheter ablation technology currently used to treat arrhythmias is mainly radiofrequency energy, and supplemented by cryoenergy. These two ablation methods have shown certain advantages in the treatment of arrhythmias, but they also have corresponding limitations. For example, ablation energy lacks selectivity in destroying tissues in the ablation area, and relies on the adhesion force of the catheter, which may cause certain damage to the adjacent esophagus, coronary arteries, and phrenic nerves. Therefore, it has become a research focus to find a relevant technology of fast, safe, and efficient ablation energy to complete and achieve durable pulmonary vein isolation without damaging adjacent tissues.

Pulsed electric field ablation technology is a new ablation method using pulsed electric field as energy. As a non-thermal ablation technology, it has increasingly attracted attention in clinical applications. In pulsed electric field ablation technology, mainly by generating a high-voltage pulsed electric field to release extremely high energy in a short period of time, a large number of irreversible micropores will be generated on cell membranes and even intracellular organelles such as the endoplasmic reticulum, mitochondria, cell nuclei, etc., and thus the apoptosis of diseased cells is caused, thereby achieving the expected therapeutic purpose.

For example, catheter ablation with the goal of isolating pulmonary vein electrical signals is the most commonly used method in the treatment of atrial fibrillation. In pulmonary vein ablation, the degree of attachment between an electrode of the multi-electrode ablation catheter and the tissue and the alignment angle between the catheter and the pulmonary veins (better alignment ensures that there is a uniform degree of attachment between all electrodes and tissues) play a decisive role in the ablation effect. Good attachment and alignment not only improve ablation results but also reduce the incidence of adverse events. However, there is currently no reliable technology that allows users to learn the attachment status of the electrodes, i.e., it is impossible to accurately know the degree of attachment and uniformity of the ablation electrodes.

SUMMARY

In order to solve the problems in the prior art, this application provides a pulsed electric field multi-electrode ablation apparatus. The technical solutions for this application are as follows:

1. A pulsed electric field multi-electrode ablation apparatus, comprising: an ablation catheter, which comprises a catheter and three or more electrodes arranged on the catheter; a pulse energy generator, which is electrically connected to the electrodes; and an impedance measurement component, which is electrically connected to the electrodes; wherein the pulse energy generator can generate a pulse wave between any two of the electrodes; and the impedance measurement component can detect an impedance between any two of the electrodes, and/or an impedance between any one of the electrodes and an external electrode.

2. The apparatus according to item 1, wherein the catheter is ring-shaped.

3. The apparatus according to item 1, wherein the impedance measurement component detects the impedance between any two of the electrodes to obtain an impedance value.

4. The apparatus according to item 1, wherein the pulse energy generator can generate a pulse wave between any adjacent two of the electrodes.

5. The apparatus according to item 1, wherein the impedance measurement component detects the impedance between any adjacent two of the electrodes.

6. The apparatus according to item 1, wherein the number of the electrodes is 3-12.

7. The apparatus according to item 3, wherein the apparatus also comprises an analysis system that receives the impedance value and obtains an attachment status of each of the electrodes based on the impedance value.

8. The apparatus according to item 7, wherein the analysis system is preset with a first threshold; the analysis system compares the impedance value with the first threshold to obtain a first comparison result; and the analysis system obtains an information that each of the electrodes is attached or not based on the first comparison result.

9. The apparatus according to item 7, wherein the analysis system is preset with a second threshold and a third threshold, and the third threshold is smaller than the second threshold; the analysis system compares the impedance value with the second threshold to obtain a second comparison result; the analysis system compares the impedance value with the third threshold to obtain a third comparison result; and the analysis system obtains an information that each of the electrodes is attached or not based on the second comparison result and the third comparison result.

10. The apparatus according to item 7, wherein the analysis system is preset with a fourth threshold; the analysis system compares a maximum value with a minimum value of the impedance values to obtain a first impedance range; the analysis system compares the first impedance range with the fourth threshold to obtain a fourth comparison result; and the analysis system obtains an information of attachment uniformity of each of the electrodes based on the fourth comparison result.

11. The apparatus according to item 7, wherein the analysis system is preset with a fifth threshold and a sixth threshold, wherein the fifth threshold is less than the sixth threshold; the analysis system compares the maximum value with the minimum value of the impedance values to obtain a second impedance range; the analysis system compares the second impedance range with the fifth threshold to obtain a fifth comparison result; the analysis system compares the second impedance range with the sixth threshold to obtain a sixth comparison result; and the analysis system obtains an information of attachment uniformity of each of the electrodes based on the fifth comparison result and the sixth comparison result.

12. The apparatus according to any one of items 7 to 11, wherein the apparatus further comprises a display; and the analysis system outputs the attachment status to the display.
13. The apparatus according to item 1, wherein a duration of a single pulse ablation performed by the apparatus is less than 0.2 seconds.
14. The apparatus according to item 13, wherein the pulse energy generator can generate a bidirectional pulse wave between any two of the electrodes.
15. The apparatus according to item 13, wherein a voltage amplitude range for generating the pulse wave between any two of the electrodes by the pulse energy generator is ±(600-1400V).
16. The apparatus according to item 13, wherein a wave width of the pulse wave generated between any two of the electrodes by the pulse energy generator is 2-20 microseconds.

In this application, accurate information of the attachment condition of the electrodes can be provided to users by detecting the impedance between electrodes (including the impedance between the electrodes on the catheter, and the impedance between the electrode on the catheter and an external electrode), so that the attachment status of the electrodes can be adjusted to an ideal state. Moreover, this application further provides a corresponding analysis system to help users quickly and intuitively understand the attachment condition of the electrodes. In addition, this application also provides pulse parameters for ablation treatment, thereby ensuring safety while achieving good therapeutic effects. Therefore, through the above technical solutions of the present application, the attachment status of the electrodes can be ensured, and a more ideal therapeutic effect can be achieved after the pulse wave is released between the electrodes by a pulse energy generator.

The above description is only an overview of the technical solutions of the present application. In order to make the technical means of the present application more clear and understandable to the extent that those skilled in the art can implement them according to the contents of the specification of the present application, and in order to achieve the above and other purposes, the features and advantages of the present application can be more clearly understood, and they are illustrated below with particular embodiments of the present application.

BRIEF DESCRIPTION OF THE DRAWINGS

FIG. 4.

REFERENCE NUMBERS IN THE DRAWINGS

1. Ablation catheter; 1100, catheter; 1201-1210, first electrode to tenth electrode;
2. Monitor; 3. Touch screen for controlling; 4. Host for ablation instrument; 5. Cart; 6. Storage basket;
A. Pulmonary vein orifice; B. Myocardial tissue.

DETAILED DESCRIPTION

The following embodiments of the present application are only used to illustrate specific implementations of the present application, and they cannot be understood as limitations of the present application. Any other changes, modifications, substitutions, combinations, and simplifications that do not deviate from the spirit and principles of this application will be regarded as equivalent substitutions, and they fall within the protection scope of this application.

Figure 1:
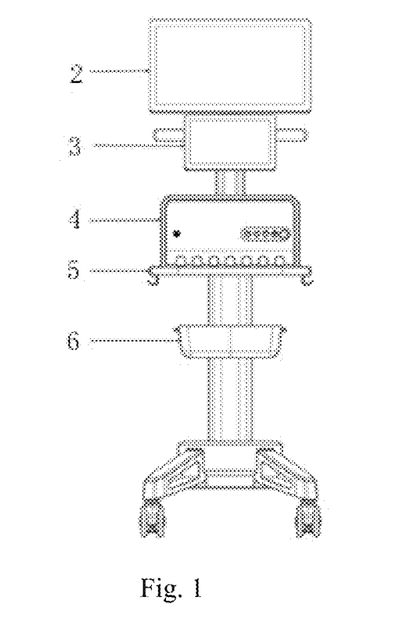
FIG. 1: a schematic front view of a pulsed electric field multi-electrode ablation apparatus.
Figure 2:
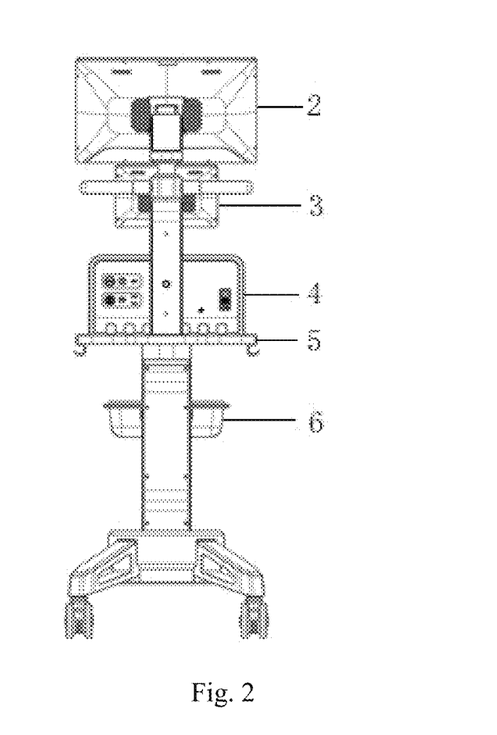
FIG. 2: a schematic rear view of a pulsed electric field multi-electrode ablation apparatus.
Figure 3:
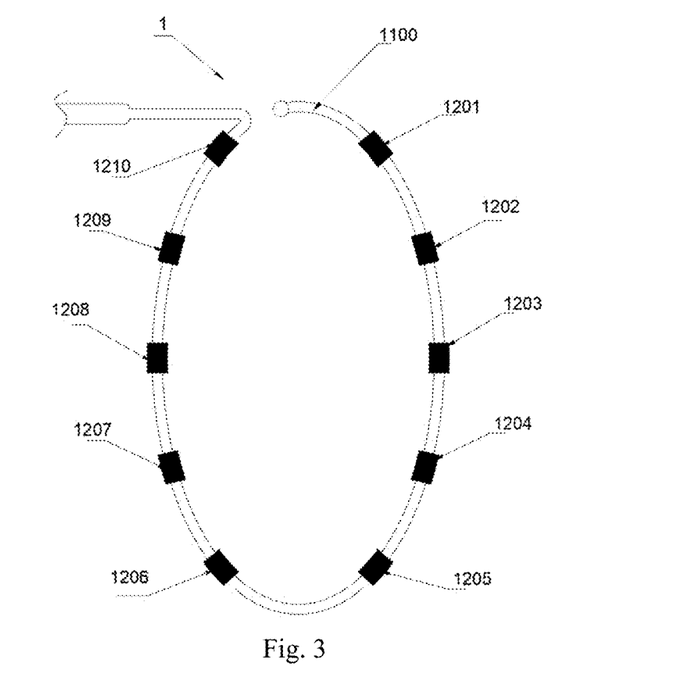
FIG. 3: a structural diagram of an ablation catheter.

This embodiment provides a pulsed electric field multi-electrode ablation apparatus, as shown in FIGS. 1-5, comprising: an ablation catheter 1, which comprises a catheter 1100 and three or more electrodes arranged on the catheter 1100; particularly, as shown in FIG. 3, in this embodiment, ten electrodes (the first electrode 1201 to the tenth electrode 1210) are provided and they are evenly arranged on the catheter 1100; a pulse energy generator, which is electrically connected to the electrode; and an impedance measurement component, which is electrically connected to the electrode; wherein the pulse energy generator can generate a pulse wave between any two of the electrodes; and the impedance measurement component can detect an impedance between any two of the electrodes and/or an impedance between any one of the electrodes and an external electrode.

In another series of patent application documents of the applicant, such as Chinese patent applications CN113768612A (titled "High-voltage transmitting circuit for catheter, and ablation tool"), CN 113648044A (titled "High-voltage transmitting circuit for catheter, and ablation tool"), CN 113648045A (titled "High-voltage transmitting circuit for catheter, and ablation tool"), etc., technical solutions that pulse waves may be generated between any two of the electrodes by the pulse energy generator are provided, thus they belong to prior art and will not be described again in this application.

The impedance measurement component can be an existing resistance tester or impedance measuring instrument, etc. Therefore, the impedance measurement component itself or its detection principle, structure, etc. also belong to prior art and will not be described again in this application. As described above, the technical solutions on how to realize generation of the pulse wave between any two electrodes are disclosed in other patent application documents of the applicant, thus those skilled in the art may know how to realize the electrical connection between any two electrodes through the impedance measurement component of the present application based on the circuits therein, and detect the impedance. Particularly, the control circuit 130, the first switch circuit 140 and the second switch circuit 150 as shown in FIG. 7 of the CN113768612A document, and the first switch circuit 130, the second switch circuit 140 and the control circuit 150 in FIG. 2 of the CN113648045A, and so on are used, thereby realizing the impedance measurement component to electrically connect any two electrodes and detect impedance. Therefore, in this application, the particular embodiments in which the impedance measurement component can detect the impedance between any two of the electrodes and/or the impedance between any one of the electrodes and an external electrode will not be described again.

When ablation treatment is performed through an ablation catheter, the impedance between an electrode attached to the tissue and the other electrode is greater than that between an electrode not attached to the tissue (e.g. an electrode in the blood) and the other electrode. That is, generally speaking, the more an electrode attached the tissue (better attachment), the greater the impedance between it and the other electrode.

Therefore, the attachment status of an electrode can be known by detecting the impedance between the electrodes on the catheter 1100; alternatively, an electrode (external electrode) can be attached outside the body, and the impedance between an electrode on the catheter 1100 and the external electrode is detected, so that the attachment status between the electrode on the catheter 1100 and the tissue is known.

Figure 4A:
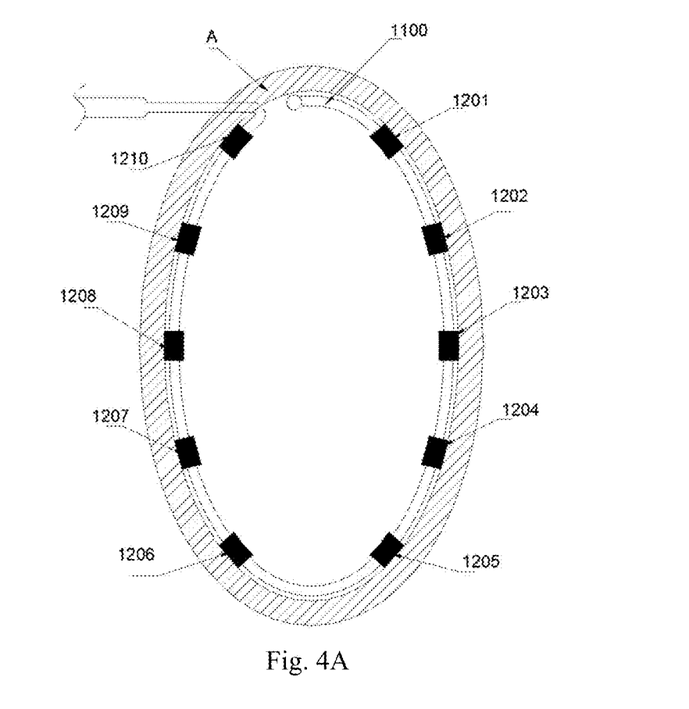
FIG. 4A, a schematic diagram of the ablation catheter evenly attaching to the pulmonary vein orifice.
Figure 4B:
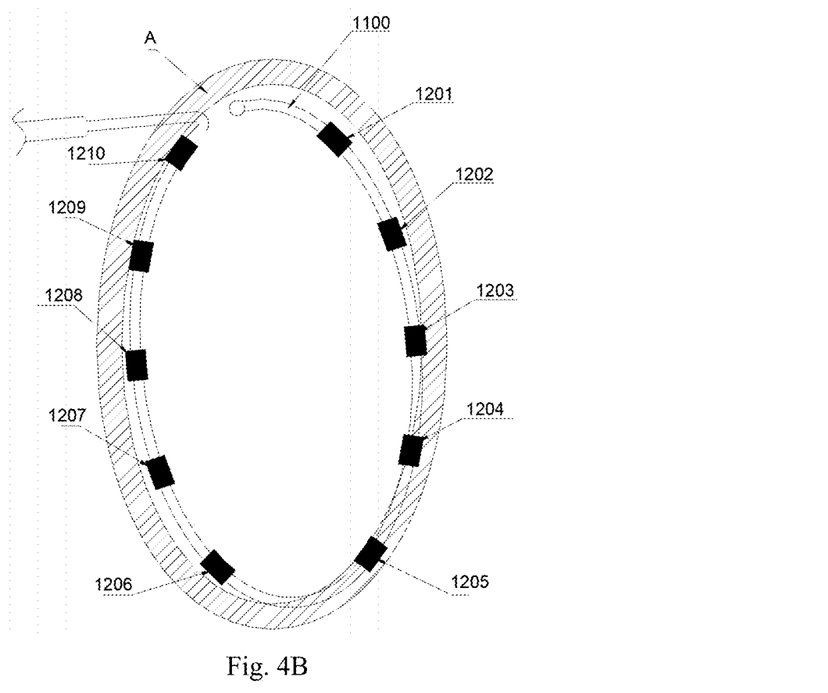
FIG. 4B, a schematic diagram of the ablation catheter not evenly attaching to the pulmonary vein orifice.

For example, when ablation treatment is performed at pulmonary vein orifice (as shown in FIG. 4B), ten electrodes are provided on the catheter, and an electrode (external electrode) can be attached outside the body, and thus the impedance between an electrode on the catheter and the external electrode is detected. The attachment status of each electrode on the catheter can be known based on the magnitude and the difference of the detected impedance. For example, based on the magnitude of the impedance, it can be known whether one, some, or all of the electrodes on the detection catheter 1100 are attached; furthermore, based on the difference between the impedances, it can be known whether the electrodes are evenly attached (the smaller the difference, the more uniform the attachment).

Similarly, the impedance between the electrodes on the catheter can also be detected. Based on the magnitude and differences of the detected impedance, the attachment status of each electrode on the catheter can be known.

In addition, as shown in FIGS. 1-2, the pulsed electric field multi-electrode ablation apparatus according to the present application may also comprise a monitor 2, a touch screen for controlling 3, a cart 5 and a storage basket 6. Particularly, the pulse energy generator and the impedance measurement component are arranged in the host for ablation instrument 4. Therefore, the impedance value detected in this embodiment can provide the user with accurate information about the attachment status (such as whether it is in an attached state, whether the attachment is uniform, etc.), so that the user can make the attachment status of the electrodes closer to the ideal state, thereby obtaining a more ideal therapeutic effect after releasing the pulse wave between the electrodes by the pulse energy generator.

Figure 5:
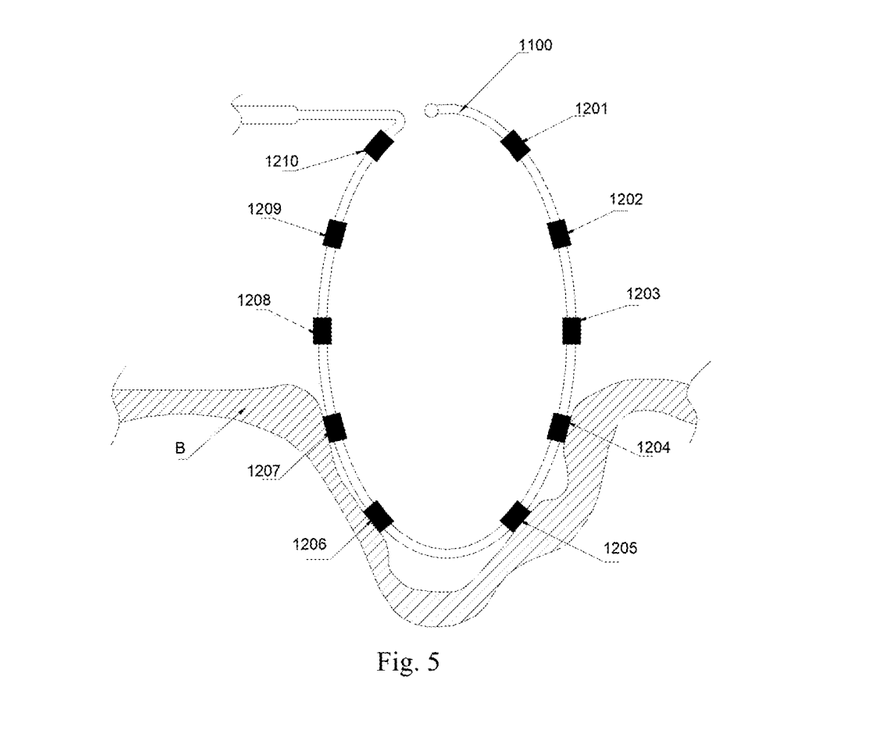
FIG. 5: a schematic diagram of the ablation catheter attaching to myocardial tissue.

In one embodiment, as shown in FIGS. 3, 4A, and 5, the catheter 1100 is ring-shaped. Then, when the catheter 1100 is ring-shaped, as shown in FIG. 4A, it can be well attached to the tubular tissue (such as the tissue in pulmonary vein orifice A); alternatively, it can be attached to the tissue in the larger cavity (myocardial tissue B as shown in FIG. 5) through one side of the catheter 1100, then the ablation treatment is performed. Therefore, the catheter can be applied to a wider range of treatment scenarios.

In one embodiment, the impedance measurement component detects the impedance between any two of the electrodes to obtain an impedance value.

This embodiment is a preferred technical solution of the above embodiment. The impedance measurement component can detect the impedance between any two of the electrodes in the ablation catheter 1. Compared with the above technical solution of attaching an electrode outside the body, in this embodiment, it does not need to attach an additional electrode outside the body, and it makes the operation easier. Moreover, the electrodes in this embodiment are all located near the site to be treated by ablation. Therefore, the detected impedance values can better reflect local attachment status of the electrodes during ablation treatment. The differences between the impedance values caused by the inconsistent attachment status of various electrodes are more obvious, so that the feedback of the attachment status of the electrodes (whether it is attached, whether the attachment is uniform, etc.) is closer to the actual situation.

Particularly, if ablation treatment is performed at pulmonary vein orifice, when the electrodes are not attached well (as shown in FIG. 4B), it will be detected that the impedance between the third electrode 1203 and the fourth electrode 1204, and the impedance between the fourth electrode 1204 and the fifth electrode 1205 is obviously large, while the impedance between the sixth electrode 1206 and the seventh electrode 1207, the impedance between the seventh electrode 1207 and the eighth electrode 1208, and the impedance between the eighth electrode 1208 and the ninth electrode 1209 is obviously small. Based on the detected impedance values, the user can clearly and intuitively understand that the ablation catheter 1 at the pulmonary vein orifice is in a state shown in FIG. 4B, so that the position of the ablation catheter 1 can be adjusted until it reaches the attached state shown in FIG. 4A so as to perform ablation treatment, thereby achieving a more ideal treatment effect. In addition, when ablation treatment is performed by only one side of the ablation catheter 1 as shown in FIG. 5, the impedance between electrodes at the side which is not used for ablation treatment (such as the first electrode 1201 to the third electrode 1203, and the eighth electrode 1208 to the tenth electrode 1210) is obviously small, while the impedance between the electrodes used for ablation treatment (such as the fourth electrode 1204 to the seventh electrode 1207) is large, then the user can know positions of the electrodes used for ablation treatment in the above way, and adjust them to an ideal state, and can accurately controll the pulse wave to be released between only electrodes used for ablation treatment, thereby achieving the ablation treatment with better effect.

In one embodiment, the pulse energy generator can generate a pulse wave between any adjacent two of the electrodes.

This embodiment provides a specific solution for releasing a pulse wave, wherein the pulse energy generator only generates the pulse wave between the adjacent two of the electrodes, such as between the first electrode 1201 and the second electrode 1202, and/or between the first electrode 1201 and the tenth electrode 1210, so that each electrode can be more simply and accurately controlled to release pulse waves evenly for ablation treatment.

In one embodiment, the impedance measurement component detects the impedance between any two adjacent electrodes.

This embodiment provides a specific solution for detecting impedance, wherein only the impedance between the adjacent two of the electrodes, such as between the first electrode 1201 and the second electrode 1202, and/or between the first electrode 1201 and the tenth electrode 1210, is detected, so that the detected impedance values continuously reflect the attachment status of the electrodes of the ablation catheter 1, which make it easier for the user to understand the attachment status of the electrodes for convenience of treatment.

In one embodiment, the number of the electrodes is 3-12, preferably 3-10.

The arrangement of 3-12 electrodes, particularly 3-10 electrodes, can make the distance between the electrodes appropriate, thereby facilitating the electrodes to release pulse waves for ablation treatment.

In one embodiment, the apparatus further comprises an analysis system.

Particularly, the analysis system can be installed on an analysis assembly, which can be a microcomputer, etc., and can specifically be composed of a processor, memory, storage, etc., and can use existing computers, etc., which will not be described again here;

wherein the analysis system receives the impedance values, and obtains the attachment status of the electrodes (such as whether the electrodes are in an attached state, whether each electrode is in uniform attachment, etc.) based on the impedance values.

Figure 6:
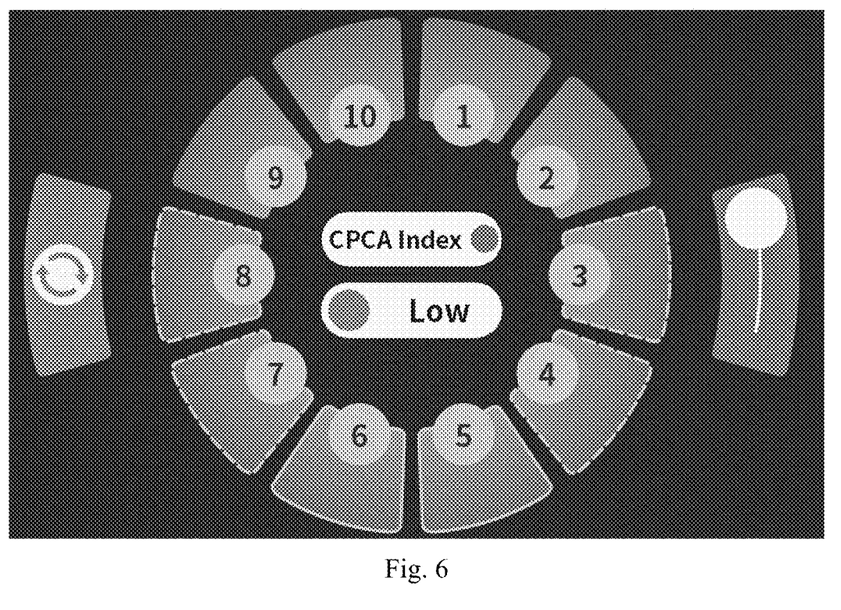
FIG. 6: a schematic diagram of the display interface of a monitor.

Then, this embodiment provides an analysis assembly (such as a computer, etc.) and its analysis system for receiving and processing each impedance value detected by the impedance measurement component, and the attachment status (such as whether it is in an attached state, whether each electrode is in uniform attachment) is output, as shown in FIG. 6, an interface for output to the monitor is provided. This facilitates the user to understand the status of the ablation catheter 1 more quickly and intuitively, and allows the user to accurately and quickly adjust the positions of the ablation catheter 1 and each electrode, thereby improving treatment efficiency and ensuring treatment effects.

In one embodiment, the analysis system is preset with a first threshold; wherein the impedance value is compared with the first threshold value by the analysis system to obtain a first comparison result. Particularly, the magnitude of the impedance value can be compared with that of the first threshold value, or the impedance value can be compared with the first threshold value to obtain a difference, or the impedance value can be compared with the first threshold value to obtain a ratio (can be expressed as a percentage, decimal, fraction), etc., thereby obtaining the first comparison result reflecting the magnitude, difference or ratio.

The analysis system obtains an information that the electrode is attached or not according to the first comparison result, and can further output the information of being attached or not to a monitor or the like for display.

The first threshold preset in this embodiment can be the impedance value between the electrodes when the electrodes are attached well. Therefore, the analysis system compares an impedance value with the first threshold to obtain the first comparison result, so as to determine whether the electrodes are attached.

More particularly, the following description is made by comparing the magnitude between an impedance value and the first threshold value.

If the first comparison results related to an electrode all show that the impedances between it and other electrodes are less than the first threshold, the analysis system determines that the electrode is not attached well and outputs the information that the electrode is not attached well. As long as the first comparison results related to an electrode show that the impedance between it and at least one other electrode is equal to or greater than the first threshold, the analysis system determines that the electrode is attached well and outputs the information of good attachment.

For example, as shown in FIG. 4B, if the first electrode 1201 is not attached well, the impedance between it and any other electrode will be less than the first threshold. Take the third electrode 1203 as an example, the impedance between it and the fourth electrode 1204, the fifth electrode 1205, the ninth electrode 1209, or the tenth electrode 1210 is greater than the first threshold; while the impedance between it and the first electrode 1201, the second electrode 1202, the sixth electrode 1206, the seventh electrode 1207, or the eighth electrode 1208 is less than the first threshold, but as long as the impedance value between the third electrode 1203 and one of the other electrodes (such as the fourth electrode 1204, the fifth electrode 1205, the ninth electrode 1209, or the tenth electrode 1210) is equal to or greater than the first threshold, it can be determined that the third electrode 1203 is attached well. This allows accurate output of the information that it is attached or not.

Of course, those skilled in the art know that the attachment status can also be determined by comparing the impedance value and the first threshold in the difference or ratio through a method similar to the above for comparing the magnitude, which will not be described again here.

Through the technical solution of this embodiment, the user can quickly and intuitively understand which electrodes are attached well, and which electrodes are not attached well, so as to facilitate the user to adjust the positions of the ablation catheter 1 and each electrode more accurately and quickly, thereby improving the treatment efficiency and guaranteeing the treatment effect.

In one embodiment, the analysis system is preset with a second threshold and a third threshold, wherein the third threshold is smaller than the second threshold;

the analysis system compares the impedance value with the second threshold (such as the above mentioned comparison relating to magnitude, difference, or ratio, etc.) to obtain the second comparison result;

the analysis system compares the impedance value with the third threshold (such as the above mentioned comparison relating to magnitude, difference, or ratio, etc.) to obtain the third comparison result; and the analysis system obtains the information that the electrode is attached or not based on the second comparison result and the third comparison result, and can output the information of being attached or not to a monitor or the like for display.

The second threshold preset in this embodiment can be the impedance value between the electrodes when they are attached well (that is, the same as the previous embodiment). The third threshold preset in this embodiment is the impedance value between the electrodes when they are in an attached state but not attached well.

Similar to what was described in the previous embodiment, the analysis system can obtain information that which electrodes are attached well based on the second comparison result. Similar to the preset second threshold, through the third comparison result, the analysis system can obtain which electrodes are in an attached state but not attached well. At the same time, the analysis system can determine that the remaining electrodes are not in an attached state. Therefore, the analysis system can output the information that it is attached or not (attached well/in an attached state but not attached well/not in an attached state).

Of course, those skilled in the art know that the attachment status can also be determined by comparing the impedance value and the second threshold or the third threshold respectively to obtain a difference or ratio, etc.

through a method similar to the above comparison of the magnitude, which will not be repeated herein.

In addition, the analysis system can output the information that an electrode is attached or not (attached well/in an attached state but not attached well/not in an attached state) to a monitor for display. As shown in FIG. 6, the marks 1 to 10 in the interface represent the first electrode 1201 to the tenth electrode 1210 respectively. When an electrode is attached well, it can be displayed that the electrode is surrounded by a solid line (e.g., the marks 5 and 6 respectively corresponding to such two electrodes). When an electrode is an attached state but not attached well, it can be displayed that the electrode is surrounded by a dotted line (e.g., the marks 3, 4, 7, and 8 respectively corresponding to such four electrodes). When an electrode is not in an attached state, it can be displayed that the electrode is not surrounded by any line segment (e.g., the marks 1, 2, 9, and 10 corresponding to such four electrodes). This allows the user to intuitively and quickly understand the attachment status of each electrode.

Through the technical solution of this embodiment, a preset third threshold is added to further optimize the previous embodiment, so that the user can quickly and intuitively understand which electrodes are attached well, which electrodes are in an attached state but not attached well, and which electrodes are not in an attached state. This allows the user to adjust the positions of the ablation catheter 1 and each electrode more accurately and quickly, thereby improving the treatment efficiency and ensuring the treatment effect.

In one embodiment, the analysis system is preset with a fourth threshold;
the analysis system compares the maximum value with the minimum value of the impedance values (such as the above mentioned comparison relating to magnitude, difference, or ratio, etc.) to obtain a first impedance range;
the analysis system compares the first impedance range with the fourth threshold (such as the above mentioned comparison relating to magnitude, difference, or ratio, etc.) to obtain a fourth comparison result; and
the analysis system obtains the information of attachment uniformity of each electrode based on the fourth comparison result, and can output the information of attachment uniformity to a monitor or the like for display.

The following is explained by comparing the maximum value with the minimum value of the impedance values to obtain a difference, and comparing the first impedance range with magnitude of the fourth threshold.

The fourth threshold in this embodiment is preset to be slightly larger than the value of the first impedance range when each electrode is evenly attached (the state shown in FIG. 4A). Then, when the fourth comparison result is that the first impedance range is equal to or less than the fourth threshold, the analysis system outputs the information that each electrode is evenly attached. When the fourth comparison result is that the first impedance range is greater than the fourth threshold, then the analysis system outputs the information that the electrodes are not evenly attached (the state as shown in FIG. 4B).

The analysis system can output the information that each electrode has been evenly attached/the electrodes have not been evenly attached to a monitor, so that the user can intuitively understand the status of the attachment uniformity of the electrodes.

Of course, those skilled in the art know that the information of the attachment uniformity (evenly attached/not evenly attached) can also be obtained by comparing the maximum value with the minimum value of the impedance values to obtain a ratio, and comparing the first impedance range with the fourth threshold obtain a difference/ratio, which is similar to the above content and thuswill not be repeated again herein.

Through the technical solution of this embodiment, the user can quickly and intuitively understand the information of the attachment uniformity (evenly attached/not evenly attached), so that the user may adjust the positions of the ablation catheter 1 and each electrode more accurately and quickly, thereby improving the treatment efficiency and ensuring the treatment effect.

In one embodiment, the analysis system is provided with a fifth threshold and a sixth threshold, wherein the fifth threshold is less than the sixth threshold;
the analysis system compares the maximum value with the minimum value of the impedance values (e.g., the above mentioned comparison relating to difference, ratio, etc.) to obtain a second impedance range;
the analysis system compares the second impedance range with the fifth threshold (e.g., the above mentioned comparison relating to magnitude, difference, ratio, etc.) to obtain a fifth comparison result;
the analysis system compares the second impedance range with the sixth threshold (e.g., the above mentioned comparison relating to magnitude, difference, ratio, etc.) to obtain a sixth comparison result; and
the analysis system obtains the information of the attachment uniformity (evenly attached/evenly attached to some extent but not an ideal state/not evenly attached), and particularly, can output the information of the attachment uniformity to a monitor or the like for display.

This embodiment is a further optimization of the previous embodiment.

Similar to the previous embodiment, firstly the description is made by comparing magnitude of the second impedance range (the difference between the maximum value and the minimum value) with that of the fifth threshold (i.e., the "fifth comparison result"), and comparing magnitude of the second impedance range with that of the sixth thresholds (i.e., the "sixth comparison result").

The fifth threshold in this embodiment is preset to be slightly larger than the value of the second impedance range when each electrode is evenly attached (consistent with the fourth threshold in the above embodiment), then when the fifth comparison result is that the second impedance range is equal to or less than the fifth threshold, the analysis system outputs the information that each electrode has been evenly attached. At the same time, this embodiment provides a sixth threshold value that is greater than the fifth threshold value. The sixth threshold value is preset to be the value of the second impedance range when each electrode in the second impedance range are evenly attached to some extent but not an ideal state. It is similar to the above mentioned, when the fifth comparison result and the sixth comparison result show that the second impedance range is greater than the fifth threshold and equal to or less than the sixth threshold, then the analysis system outputs the information that the electrodes are evenly attached to some extent but not an ideal state. When the sixth comparison result is that the second impedance range is greater than the sixth threshold, then the analysis system outputs the information that the electrodes are not evenly attached (the state as shown in FIG. 4B).

Of course, those skilled in the art know that they can also compare the maximum value with the minimum value to obtain a ratio, compare the second impedance range with the fifth threshold to obtain a difference/ratio, or compare the second impedance range with the sixth threshold to obtain a difference/ratio, so as to acquire the information of the attachment uniformity (evenly attached/evenly attached to some extent but not an ideal state/not evenly attached) and output it. Since it is similar to the above content, further details will not be given herein.

The analysis system can output the attachment information of each electrode (evenly attached/evenly attached to some extent but not an ideal state/not evenly attached) to a monitor. As shown in FIG. 6, the circles on the right side of the CPCA index in FIG. 6 are displayed in green, yellow and red, which respectively represent that an electrode has been evenly attached, has been evenly attached to some extent but not an ideal state/not evenly attached, and an electrode is not evenly attached. This makes it easy for users to quickly and intuitively understand the status of the attachment uniformity.

Through the technical solution of this embodiment, the user can quickly and intuitively understand the information of the attachment uniform (evenly attached/evenly attached to some extent but not an ideal state/not evenly attached), so that the user can adjust the positions of the ablation catheter 1 and each electrode more accurately and quickly, thereby improving the treatment efficiency and ensuring the treatment effects.

It should be noted that, based on the above content, it can be known that those skilled in the art can preset and adjust appropriate first to sixth thresholds according to actual situations, and those will not be described again herein.

In one embodiment, a duration of a single pulse ablation performed by the apparatus performs is less than 0.2 seconds.

In this application, the duration of a single pulse ablation refers to the time it takes to complete the release of pulse energy from all electrode pairs.

The total discharge time of traditional radiofrequency ablation is 10-20 minutes, but the duration of the single pulse ablation of this embodiment is less than 0.2 seconds, and the total discharge time can be shorten to about 10 seconds, while speeding up the atrial fibrillation treatment operation, it can also reduce safety concerns of traditional radiofrequency surgery. Less than 0.2 seconds of the duration of ablation allows a single-pulse ablation to be completed within the refractory period within a cardiac cycle, thereby reducing the possibility of arrhythmia and improving the safety of ablation.

In one embodiment, the pulse energy generator is capable of generating bidirectional pulse waves between any two of the electrodes.

The use of "bidirectional pulse wave" can reduce muscle tremors caused by pulse ablation, improve the tolerance of the patient, and enable pulse ablation surgery to be completed under local anesthesia.

In one embodiment, the pulse energy generator can generate a pulse wave between any two electrodes with a voltage amplitude range of ±(600V to 1400V). Within this optimized voltage range, effective ablation of the myocardium can be performed.

This embodiment provides a voltage amplitude range, which can ensure a more ideal ablation effect when the duration of the single pulse ablation is less than 0.2 seconds.

In one embodiment, the pulse energy generator can generate pulse waves between any two electrodes with a wave width of 2-20 microseconds. Under this wave width, pulse ablation can meet the ablation energy requirements, and at the same time muscle tremors caused by pulses are also reduced.

Examples

The experimental methods used below are all routine methods unless there are special requirements.

The materials and reagents used below are commercial available unless otherwise specified.

In the following Examples and Comparative Examples, with animal model (pig) experiments simulating clinical application, the applicant used the above-mentioned pulsed electric field multi-electrode ablation apparatus (10 electrodes and bidirectional pulse waves are provided in the annular ablation catheter) to perform ablation in the left atrium for pulmonary vein isolation, and perform ablation in the right atrium for superior vena cava isolation; and the ablation is performed in the left ventricle and right ventricle to detect whether arrhythmias are caused. The specific implementation is shown in the following tables (Table 1, Table 2).

TABLE 1

|  | Example 1 | Example 2 | Example 3 |
|---|---|---|---|
| Number of animals | 10 | 3 | 3 |
| Ablation area | RA/LA | RA/LA | RA/LA/RV/LV |
| Volatage of pulse wave/V | ±(600 V~1400 V) | ±(600 V~1400 V) | ±(600 V~1400 V) |
| Wave width/µs | 2-20 µs | 2-20 µs | 2-20 µs |
| Duration of a single pulse ablation/second | <0.2 seconds | <0.2 seconds | <0.2 seconds |
| Number of ablation times in the same area | 3 | 6 | 6 |

TABLE 2

|  | Comparative Example 1 |
|---|---|
| Number of animals | 1 |
| Ablation area | RA/LA/RV |
| Voltage of pulse wave/V | ±(600 V~1400 V) |
| Wave width/µs | 2-20 µs |
| Duration of a single pulse ablation duration/second | 1.8 seconds |
| Number of ablation times in the same area | 6 |

(LV: left ventricle; LA: left atrium; RV: right ventricle; RA: right atrium)

Test Results

In the above Examples 1-3, 100% electrical signal isolation of the pulmonary veins (32/32) and the superior vena cava was achieved in all 16 animals (pigs). The total number of ablation times per animal ranged 43-92, with an average number of ablation times of 63.3±13.0, and the total discharge time ranged 7.7-16.4 seconds, with an average total discharge time of 11.3±2.3 seconds. In Example 3, the intraventricular ablations were performed in three pigs, and no arrhythmia including ventricular fibrillation was induced in a total of 166 ablations.

In comparison, in Comparative Example 1, when the duration of a single pulse ablation was longer than one second, a single ablation in the right ventricle caused ventricular fibrillation to result in the death of the animal.

In addition, simultaneously using the above-mentioned pulse ablation parameters (single pulse ablation duration, bidirectional pulse wave, and voltage amplitude range and wave width of the pulse wave) can reduce systemic muscle fibrillation. The muscle fibrillations caused in a total of 1,179 ablations were not of clinical concern, and the clinicians considered that the operations can be performed under local anesthesia.

Although the embodiments of the present application have been described above, the present application is not limited to the above particular embodiments and application fields. The above particular embodiments are only illustrative and instructive, rather than restrictive. Under the inspiration of this description and without departing from the protection scope of the claims of this application, an ordinary skilled person in the art can also make many variations, which all fall within the protection scope of the present application.

What is claimed is:

1. A pulsed electric field multi-electrode ablation apparatus for ablation of a pulmonary vein orifice, comprising:
    an ablation catheter, which comprises a catheter that is ring-shaped and three or more electrodes arranged on the catheter;
    a pulse energy generator, which is electrically connected to the electrodes;
    an impedance measurement component, which is electrically connected to the electrodes; and
    an analysis system;
    wherein the pulse energy generator can generate a pulse wave between any two of the electrodes;
    the impedance measurement component detects the impedance between any adjacent two of the electrodes to obtain an impedance value;
    the analysis system receives the impedance value and obtains an attachment status of each of the electrodes based on the impedance value, wherein the attachment status includes whether the electrodes are attached and whether the electrodes are evenly attached;
    the analysis system is preset with a fourth impedance threshold; the analysis system compares a maximum value with a minimum value of the impedance values to obtain a first impedance range; the analysis system compares the first impedance range with the fourth impedance threshold to obtain a fourth comparison result; and the analysis system obtains an information of attachment uniformity of each of the electrodes based on the fourth comparison result; or,
    the analysis system is preset with a fifth impedance threshold and a sixth impedance threshold, wherein the fifth impedance threshold is less than the sixth impedance threshold; the analysis system compares a maximum value with a minimum value of the impedance values to obtain a second impedance range; the analysis system compares the second impedance range with the fifth impedance threshold to obtain a fifth comparison result; the analysis system compares the second impedance range with the sixth impedance threshold to obtain a sixth comparison result; and the analysis system obtains an information of attachment uniformity of each of the electrodes based on the fifth comparison result and the sixth comparison result.

2. The apparatus according to claim 1, wherein the pulse energy generator can generate a pulse wave between any adjacent two of the electrodes.

3. The apparatus according to claim 1, wherein the number of the electrodes is 3-12.

4. The apparatus according to claim 1, wherein the analysis system is preset with a first impedance threshold;
    the analysis system compares the impedance value with the first impedance threshold to obtain a first comparison result; and
    the analysis system obtains an information that each of the electrodes is attached or not based on the first comparison result.

5. The apparatus according to claim 1, wherein the analysis system is preset with a second impedance threshold and a third impedance threshold, and the third impedance threshold is smaller than the second impedance threshold;
    the analysis system compares the impedance value with the second impedance threshold to obtain a second comparison result;
    the analysis system compares the impedance value with the third impedance threshold to obtain a third comparison result; and
    the analysis system obtains an information that each of the electrodes is attached or not based on the second comparison result and the third comparison result.

6. The apparatus according to claim 1, wherein the apparatus further comprises a display; and
    the analysis system outputs the attachment status to the display.

7. The apparatus according to claim 1, wherein a duration of a single pulse ablation performed by the apparatus is less than 0.2 seconds.

8. The apparatus according to claim 7, wherein the pulse energy generator is configured to generate a bidirectional pulse wave between any two of the electrodes.

9. The apparatus according to claim 7, wherein a voltage amplitude range for generating the pulse wave between any two of the electrodes by the pulse energy generator is ±(600-1400V).

10. The apparatus according to claim 7, wherein a wave width of the pulse wave generated between any two of the electrodes by the pulse energy generator is 2-20 microseconds.

* * * * *